US006093701A

United States Patent [19]
Wolff et al.

[11] Patent Number: 6,093,701
[45] Date of Patent: Jul. 25, 2000

[54] METHOD FOR COVALENT ATTACHMENT OF COMPOUNDS TO GENES

[75] Inventors: Jon A. Wolff; James E. Hagstrom; Magdolna G. Sebestyén; Vladimir Budker, all of Madison, Wis.

[73] Assignee: Mirus, Inc., Madison, Wis.

[21] Appl. No.: 08/990,015

[22] Filed: Dec. 12, 1997

Related U.S. Application Data
[60] Provisional application No. 60/050,842, Jun. 26, 1997.

[51] Int. Cl.[7] .................................................. A61K 48/00
[52] U.S. Cl. ..................... 514/44; 435/69.1; 435/320.1; 435/325; 435/455; 536/23.1
[58] Field of Search .......................... 514/44; 435/320.1, 435/455, 69.1, 325; 536/23.1

[56] References Cited

U.S. PATENT DOCUMENTS

| | | | |
|---|---|---|---|
| 5,215,889 | 6/1993 | Schultz | 435/41 |
| 5,428,132 | 6/1995 | Hinsch et al. | 530/387.1 |
| 5,659,022 | 8/1997 | Kutyawin et al. | 536/22.1 |
| 5,736,392 | 4/1998 | Hawley-Nelson et al. | 435/320.1 |
| 5,770,736 | 6/1998 | Arya et al. | 546/268.1 |
| 5,786,138 | 7/1998 | Swenson | 435/6 |

FOREIGN PATENT DOCUMENTS

WO 95/28494   10/1994   WIPO .

OTHER PUBLICATIONS

Leahy et al. (Bioconjugate Chem, 7, pp. 545–551, Sep. 1996).
Cheng et al., Nucleic Acids Research, vol. 11, No. 3, 1983, pp. 659–669, 1983.
Adam, S.A. et al., "Cytosolic Proteins That Specifically Bind Nuclear Location Signals Are Receptors for Nuclear Import," *Cell* Sep. 6, 1991; vol. 66; 837–847.
Adam, S.A. et al., "Nuclear Protein Import in Permeabilized Mammalian Cells Requires Soluble Cytoplasmic Factors." *The Journal of Cell Biology* Sep. 1990; vol. 111; 807–816.
Adam, S.A. et al., "Nuclear Protein Import Using Digitonin–Permeabilized Cells." *Methods in Enzymology* 1992; vol. 219; 97–110.
Boger, D.L. et al., "CC–1065 and the duocarmycins: Unraveling the keys to a new class of naturally derived DNA alkylating agents." *Proc. Natl. Acad. Sci. USA* Apr. 1995; vol. 92: pp.3642–3649.
Brandt, J. et al. "Covalent Attachment of Proteins To Polysaccharide Carrier By Means Of Benzoquinone." *Biochimica et Biophysica Acta*, vol. 386, 1975; 196–202.
Bustamante, J.O. et al., "Nuclear pore complex ion channels (Review). " *Molecular Membrane Biology* 1994; 11; 141–150.
Chin, D.J., et al., "Rapid Nuclear Accumulation of Injected Oligodeoxyribonucleotides." *The New Biologist* Dec., 1990; Bol.2, No. 12; pp. 1091–1100.
Collas, P. Et al., "Nuclear Localization Signal of SV40 T Antigen Directs Import of Plasmid DNA into Sea Urchin Male Pronuclei In Vitro." *Molecular Reproduction and Development* 1996; 45; 431–438.

Collas, P. Et al., "Nuclear localization signals: a driving force for nuclear transport of plasmid DNA in xebrafish." *Biochem. Cell Biol.* 1997; 75; 633–640.
De Wet, J.R. et al., "Firefly Luciferase Gene: Structure and Expression in Mammalian Cells." *Molecular and Cellular Biology* Feb. 1987; p. 725–737.
Dean, D.A., "Import of Plasmid DNA into the Nucleus Is Sequence Specific." *Experimental Cell Research* 1997; 230; 293–302.
Dowty, M.E. et al., "Characterization of Biotinylated and Gold–Labeled Plasmid DNA." *Methods in Molecular and Cellular Biology* 1992; 3; 167–174.
Dowty, M.E. et al., "Plasmid DNA entry postmitotic nuclei of primary rat myotubes." *Proc. Natl. Acad. Sci. USA* May 1995; vol. 92; pp. 4572–4576.
Dworetzky, S.I. et al., "The Effects of Variations in the Number and Sequence of Targeting Signals on Nuclear Uptake." *The Journal of Cell Biology* Oct. 1988; vol. 107; 1279–1287.
Feldherr, C.M. et al., "Movement of a Karyophilic Protein through the Nuclear Pores of Oocytes." *The Journal of Cell Biology* Dec. 1984; vol. 99; 2216–2222.
Feldherr C.M. et al., "The Permeability of the Nuclear Envelope in Dividing and Nondividing Cell Cultures." *The Journal of Cell Biology* Jul. 1990; vol. 111; 1–8.
Fishman, D.M. et al., "Light Scattering Studies of Supercoiled and Nicked DNA." *Biopolymers* 1996; vol. 38; 535–552.
Forbes, D.J., "Structure and Function of the Nuclear Pore Complex." *Annu. Rev. Cell Biol.* 1992, 8; 495–527.
Fritz, J.D. et al., "Gene Transfer into Mammalian Cells Using Histone–Condensed Plasmid DNA." *Human Gene Therapy* Aug. 1, 1996; 7; 1395–1404.
Gallay, P. Et al., "Role of the Karyopherin Pathway in Human Immunodeficiency Virus Type 1 Nuclear Import." *Journal of Virology* Feb. 1996; vol. 70, No. 2; p. 1027–1032.
Garcia–Bustos, J. Et al., "Nuclear protein localization." *Biochimica et Biophysica Acta* 1991; 1071; 83–101.
Garcia–Ramirez, M. Et al., "Condensation of DNA by Basic Proteins Does Not Depend on Protein Composition." *Biopolymers* 1994; vol. 34; 285–292.
Gershon, H. Et al., "Mode of Formation and Structural Features of DNA–Cationic Liposome Complexes Used for Transfection." *Biochemistry* 1993; 32; 7143–7151.
Goldfarb, D.S., "Nuclear transport: Proliferating pathways." *Current Biology* 1997, vol. 7, No. 1; R13–R16.
Gorlich, D. Et al., "Nucleocytoplasmic Transport." *Protein Kinesis: Science* Mar. 15, 1996; vol. 271; 1513–1518.

(List continued on next page.)

*Primary Examiner*—Scott D. Priebe
*Assistant Examiner*—Dave Trong Nguyen
*Attorney, Agent, or Firm*—Mark K. Johnson

[57] ABSTRACT

The described invention relates to methods for covalently attaching a compound to a gene. The method provides for covalently attaching compounds to genes for enhancing the cellular transport of the genes to predetermined targets, while maintaining the gene's functionality.

18 Claims, 10 Drawing Sheets

OTHER PUBLICATIONS

Hagstrom, J.E. et al., "Nuclear import of DNA in digitonin–permeabilized cells." *Journal of Cell Science* 1997; 110; 2323–2331.

Henkel, T. Et al., "Intramolecular Masking of the Nuclear Location Signal and Dimerization Domain in the Presursor for the p50 NF–KB Subunit." *Cell* Mar. 20, 1992; vol. 68; 1121–1133.

Hubner, S. Et al., "The Protein Kenase CK2 Site (Ser 111/112) Enhances Recognition of the Simian Virus 40 Large T–antigen Nuclear Localization Sequence by Importin." *The Journal of Biological Chemistry* Jul. 4, 1997; vol. 272, No. 27; pp. 17191–17195.

Hurley, L.H. et al., "Nolecular Basis for Sequence–Specific DNA Alkylation by CC–1065." *Biochemistry* 1988; 27; 3886–3892.

Hurley, L.H. et al., "Sequence Specificity of DNA alkylation by the Unnatural Enantiomer of CC–1065 and Its Synthetic Analogues." *J. Am. Chem. Soc.* 1990; 112; 4633–4649.

Ibanez, M. Et al., "Spermidine–condensed DNA adn cone–shaped lipids improve delivery and expression of exogenous DNA transfer by liposomes." *Biochem. Cell Biol.* 1996; 74; 633–643.

Jans, D.A. et al., "Regulation of Protein Transport to the Nucleus: Central Role of Phosphorylation." *Physiological Reviews* Jul. 1996; vol. 76, No.3; 651–685.

Kalderon, D. Et al., "A Short Amino Acid Sequence Able to Specify Nuclear Location." *Cell* Dec. 1984; vol. 39; 499–509.

Kaneda, Y. et al., "Icreased Expression of DNA Cointroduced with Nuclear Protein in Adult Rat Liver." *Reports* Jan. 1989; 375–378.

Kaneda, Y. et al., "Increased Expression of DNA Cointroduced with Nuclear Protein in Adult Rat Liver." *Science* Jan. 20, 1989; vol. 243; 375–378.

Kasamatsu, H. Et al., "How Do Animal DNA Viruses Get to the Nucleus?" *Annu. Rev. Microbiol.* 1998; 52; 627–86.

Kose, S. Et al., "Ran–unassisted Nuclear Migration of a 97–kD Componet of Nuclear Pore–targeting Complex." *The Journal of Cell Biology* Nov. 17, 1997; vol. 139, No. 4; 841–849.

Lanford, R.E. et al., "Induction of Nuclear Transport with a Synthetic Peptide Homologous to the SV40 T Antigen Transport Signal." *Cell* Aug. 15, 1986; vol. 46; 575–582.

Langle–Rouault, F. Et al., "Up to 100–Fold Increase of Apparent Gene Expression in the Presence of Epstein–Barr Virus *oriP* Sequences and EBNA1: Implications if the Nuclear Import of Plasmids." *Journal of Virology* Jul. 1998; vol. 72, No. 7; p. 6181–6185.

Leonetti, J.P. et al., "Intracellular distribution of microinjected antisense oligonucleotides." *Proc. Natl. Aced. Sci. USA* Apr. 1991; vol. 88; 2702–2706.

Levitt, N. et al., "Definition of an efficient synthetic poly(A) site." *Genes and Development* 1989; 3; 1019–1025.

Lukhtanov, E.A. et al., "Rapid and efficient hybridization–triggered crosslinking within a DNA duplex by and oligodeoxyribonucleotide bearing a conjugated cyclopropapyrroliondole." *Nucleic Acids Research* 1996; vol. 24, No. 4; 683–687.

Lukhtanov, E.A. et al., "Sequence and Structure Dependence of the Hybridization–Triggered Reaction of Oligonucleotides Bearing Conjugated Cyclopropapyrroloindole." *J. Am. Chem. Soc.* 1997; 119; 6214–6225.

Mattaj, I.W. et al., "Nucleocytoplasmic Transport: The Soluble Phase." *Annu. Rev. Biochem.* 1998; 67; 265–306.

Mirzayans, R. Et al., "Differential expression and stability of foreign genes introduces into human fibroblasts by nuclear versus cytoplasmic microinjection." *Mutation Research* 1992; 281; 115–122.

Moroianu, J. Et al., "Nuclear protein import: Ran–GTP dissociates the karyopherin heterodimer by displacing _ from and overlapping binding site on _." *Proc. Natl. Acad. Sci. USA* Jul. 1996; vol. 93, pp. 7059–7062.

Nigg, E.A., "Nucleocytoplasmic transport: signals, mechanisms and regulation." *Nature* Apr. 24, 1997; vol. 386; 778–787.

Pollard, V.W. et al., "A Novel Receptor–Mediated Nuclear Protein Import Pathway." *Cell* Sep. 20, 1996; vol. 86; 985–994.

Poncet, P. et al., "Antifection: an antibody–mediated method to introduce genes into lymphoid cells in vitro and in vivo." *Gene Therapy* (1996) vol. 3; 731–738.

Radu, A. Et al., "The Peptide Repeat Domain of Nucleoporin Nup98 Functions as a Docking Site in Transport across the Nuclear Pore Complex." *Cell* Apr. 21, 1995; vol. 81; 215–222.

Rechardson, W.D. et al., "Nuclear Protein Migration Involves Two Steps: Raped Binding at the Nuclear Envelope Followed by Slowere Translocation through Nuclear Pores." *Cell* Mar. 11, 1988; vol. 52; 655–664.

Rihs, H. Et al., "The rate of nuclear cytoplasmic protein transport is determined by the casein kinase II site flanking the nuclear localization sequence of the SV40 T–antigen." *The EMBO Journal* 1991; vol. 10, No. 3; 633–639.

Sebestyen, M.G. et al., "DNA vector chemistry: The covalent attachment of signal peptides to plasmid DNA." *Nature Biotechnology* Jan. 1998; vol. 16; 80–85.

Singer, B. "DNA Damage: Chemistry, Repair, and Mutagenic Potential." *Reg. Tox. and Phar.,* 1996, vol. 23; 2–13.

Sun, D. Et al., "Effect of the CC–1065–(N3 Adenine)DNA Adduct on in Vitro DNA Synthesis Mediated by *Excherichia coli* DNA Polymerase." *Biochemistry* 1992; 31; 2822–2829.

Ternynck, T. et al. "A New Method Using P–Benzoquinone for Coupling Antigens and Antibodies To Marker Substances." *Ann. Immunol.,* 1976, vol. 127C; 197–208.

Whittaker, G. Et al., "The role of nuclear import and export in influenza virus infection."

Whittaker, G.R. et al., "Minireview: Nuclear Import and Export of Viruses and Virus Genomes." *Virology* 1998; 246; 1–23.

Wolff, J.A. et al., "The Cambrian period of nonviral gene delivery." *Nature Biotechnology* May 1998; vol. 16; 421–422.

Yoneda, Y. et al, "A Long Synthetic Peptide Containing a Nuclear Localization Signal and its flanking Sequences of SV40 T–Antigen Directs the Transport of IgM into the Nucleus Efficiently." *Experimental Cell Research* 1992; 201; 313–320.

Zanta, M.A., et al., "Gene delivery: A single nuclear localization signal peptide is sufficient to carry DNA to cell nucleus." *Proc. Natl. Acad. Sci. USA* Jan. 1999; vol. 96; pp. 91–96.

24 NLS peptide/1 kb

51 NLS peptide/1 kb

101 NLS peptide/1 kb

METHOD FOR COVALENT ATTACHMENT OF COMPOUNDS TO GENES

CROSS-REFERENCE TO RELATED APPLICATIONS (Provisional Application Ser. No. 60/050,842) (Filing Date Jun. 26, 1997)

FEDERALLY SPONSORED RESEARCH

This invention was made under a contract with an agency of the United States Government: U.S. Government agency: NIH Government contract number: R01-DK49117

Field

The described invention relates to methods for covalently attaching a compound to a gene. More specifically, the method provides for covalently attaching compounds to genes for enhancing the cellular transport of the gene while maintaining its functionality.

Background

Non-viral gene therapy is a promising approach for the treatment of acquired and genetic disorders, but requires improvements in the efficiency of gene transfer. The current paradigm for approaching this problem is to identify a limiting step in the cellular transfer of foreign genes and either avoid the step or enhance its rate. Enhancing the rate can be accomplished by using signals that mediate or enhance the cellular process. Such signals have been identified for such cellular processes as nuclear transport, cell surface binding and internalization, and endosomal release.

Nuclear Transport

One of the important steps in DNA-based gene transfer is nuclear transport, which is required for expression. Nuclear transport is the passage of molecules in and out of a nucleus, presumably via nuclear pores. This includes transport through the cytoplasm to the nucleus as well as any enhancement to nuclear entry. For example, passage of proteins into the nucleus may depend on possession of a nuclear location sequence containing five consecutive positively charged residues. The efficiency of plasmid DNA (pDNA) nucleocytoplasmic transport has been considered to be low based upon microinjection experiments in which only a small percentage of cells expressed the marker gene (Mirzayans, R., Remy, A. A. and Malcolm, P. C. 1992. Differential expression and stability of foreign genes introduced into human fibroblasts by nuclear versus cytoplasmic microinjection. *Mut. Res.* 281:115–122.). Although more recent studies in our laboratory (Dowty, M. E., Williams, P., Zhang, G. and Wolff, J. A. 1995. Plasmid DNA entry into postmitotic nuclei of primary rat myotubes. *Proc. Natl. Acad. Sci.* USA 92:4572–4576; Hagstrom, J. E., Ludtke, J. J., Bassik, M. C., Sebestyen, M. G., Adam, S. A., et al. Nuclear import of DNA in digitonin-permeabilized cells. *J. Cell Sci.* 110:2323–2331(1997)) suggest that naked DNA can enter the nuclei of non-dividing cells more proficiently than previously thought, it still is relatively inefficient in comparison to the nuclear uptake of karyophilic proteins and viral genes.

Macromolecules larger than about 60 kDa can not freely diff-use through the nuclear pore complexes (NPCs) of the nuclear envelope (Gorlich, D. and Mattaj, I. W. 1996. Nucleocytoplasmic transport. *Science* 271:1513–1518.). Structural components of the pores together with soluble cytoplasmic and nuclear factors are responsible for the highly selective active transport of certain proteins and nucleic acids into and out of the nucleus (Goldfarb, D. S. 1997. Nuclear transport-proliferating pathways. *Cur. Biol.* 7:R 13-R 16.). Proteins destined for the nucleus have one or more nuclear localization signals (NLSs) which usually contain short stretches of basic residues. Among the many putative signals identified to date, the best characterized NLS is that of the SV40 large T-antigen: Kalderon, D., Roberts, B. L., Richardson, W. D. and Smith, A. E. 1984. A short amino acid sequence able to specify nuclear location. *Cell* 39:499–509.). Synthetic peptides containing this sequence have been conjugated to different non-karyophilic proteins, causing their efficient nuclear accumulation (Goldfarb, D. S., Gariépy, J., Schoolnik, G. and Komberg, R. D. 1986. Synthetic peptides as nuclear localization signals. *BioEssays* 322:641–644.). Many other NLS's have been derived from the plethora of cellular and viral nuclear localilzing proteins.

Digitonin-permeabilized cells (Adam, S. A., Sterne-Marr, R. and Gerace, L. 1992. Nuclear protein import using digitonin-permeabilized cells. *Meth. Enzymol.* 219:97–111.) have played an important role in elucidating the mechanism of nuclear transport and have enabled the identification of several soluble factors such as the NLS receptor (karyopherin α), p97 (karyopherin β), and the GTPase Ran (Nigg, E. 1997. Nucleocytoplasmic transport: signals, mechanisms and regulation. *Nature* 386:779–787.).

Certain macromolecules which do not have their own NLS can still accumulate in the nucleus by forming complexes with karyophilic molecules (piggyback transport) (Jans, D. A. and Hubner, S. 1996. Regulation of protein transport to the nucleus: central role of phosphorylation. *Physiological Rev.* 76:651–685.). The trafficking of ribonucleic acids into and out of the nucleus is mediated by signal-bearing RNA binding proteins, like the Sm proteins in snRNP complexes, or hnRNP A1 on exported mature mRNA molecules (Pollard, V. W., Michael, W. M., Nakielny, S., Siomi, M. C., Wang, F., et al. 1996. A Novel Receptor-Mediated Nuclear Protein Import Pathway. *Cell* 86:985–994.). Similarly, proteins carrying nuclear localization signals have been proposed to play a crucial role in making viral infection efficient by helping the nuclear entry of viral DNA or RNA (Whittaker, G., Bui, M. and Helenius, A. 1996. The role of nuclear import and export in influenza virus infection. *Trends Cell Biol.* 6:67–71.).

Relying on the principle of piggyback transport, several non-covalent DNA/protein complexes have been tested for augmented nuclear import. The DNA binding high mobility group-1 protein has been reported to increase the rate of DNA nuclear entry when co-introduced with pDNA/ liposome complexes, but it did not increase the final amount of nuclear foreign DNA or the final level of expression (Kaneda, A., Iwai, K. and Uchida, T. 1989. Increased expression of DNA cointroduced with nuclear protein in adult rat liver. *Science* 243:375–378.). In comparison, the inclusion of a recombinant, SV40 NLS-containing histone H1 protein in pDNA/cationic liposome complexes substantially enhances expression not by enabling nuclear uptake but by increasing cellular uptake of the pDNA. Gene transfer into mammalian cells using histone-condensed plasmid DNA. *Hum. Gene Ther.* 7:1395–1404.). Recently, increased uptake of non-covalent NLS-peptide DNA complexes has been reported in sea urchin pronuclei (Collas, P. and Alestrom, P. 1996. Nuclear localization signal of sv40 t antigen directs import of plasmid DNA into sea urchin male pronuclei in vitro. *Mol. Reprod. Dev.* 45:431–438.). However, pDNA complexes formed with the same NLS peptide under identical conditions failed to enter HeLa cell nuclei in the digitonin-permeabilized cell assay. Furthermore, we have studied the nuclear transport of fluorescent pDNA non-covalently bound to NLSs via a variety of DNA-binding compounds or by using biotinylated DNA complexed with NLS-Streptavidin. None of these interactions enhanced the nuclear accumulation of fluorescent DNA to a microscopically detectable level in microinjected or digitonin permeabilized cells.

Cellular Targeting

A variety of ligands have been used to target drugs and genes to specific cellular receptors. Binding of these ligands to these receptors typically initiates endocytosis. Previous efforts have used the following ligands galactose ( for asialoglycoprotein receptor), mannose, folate, EGF, FGF, LDL, transferrin, insulin, IGF-I, IGF-II, immunoglobin Fc, polymeric immunoglobin, and polyanions for scavenger receptor (Y. Kato and Y Sugiyama. Critical Reviews in Therapeutic Drug Carrier Systems 14:287–331, 1997). A recent review article states that gene delivery has been attached to these ligands only by non-covalent linkers such a polylysine, biotin/avidin, and immunoliposomes (Y. Kato and Y Sugiyama. Critical Reviews in Therapeutic Drug Carrier Systems 14:287–331, 1997). Ligands could also be used for DNA delivery that bind to receptors that are not endocytosed. For example peptides containing RGD peptide sequence that bind integrin receptor could be used. In addition viral proteins could be used to bind cells. Lipids and steroids could be used to directly insert into cellular membranes.

Intracellular Compartment Release

The other cellular transport step that has attracted attention for gene transfer is that of DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Chemicals such as chloroquine, bafilomycin or Brefeldin A1. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal compartment into the trans-Golgi network (TGN) to form tubules. Bafilomycin $A_1$, a macrolide antibiotic is a more specific inhibitor of endosomal acidification and vacuolar type $H^+$-ATPase than chloroquine. The ER-retaining signal (KDEL sequence) has been proposed to enhance delivery to the endoplasmic reticulum and prevent delivery to lysosomes (S. Seetharam et al. J. Biol. Chem. 266:17376, 1991).

Viruses such as adenovirus have been used to induce gene release from endosomes or other intracellular compartments (D. Curiel, Agarwal, S., E. Wagner, and Cotten, M. PNAS 88:8850, 1991). Rhinovirus has also been used for this purpose (W. Zauner et al. J. Virology 69:1085–92, 1995). Viral components such as influenza virus hemagglutinin subunit HA-2 analogs has also been used to induce endosomal release (E. Wagner et al. PNAS 89:7934, 1992). Amphipathic peptides resembling the N-terminal HA-2 sequence has been studied (K. Mechtler and E. Wagner, New J. Chem. 21:105–111, 1997). Parts of the pseudonmonas exotoxin and diptheria toxin have also been used for drug delivery (I. Pastan and D. FitzGerald. J Bio. Chem. 264:15157, 1989). A variety of synthetic amphipathic peptides have been used to enhance transfection of genes (N. Ohmori et al. Biochem. Biophys. Res. Commun. 235:726, 1997).

SUMMARY

Previous efforts at enabling the transfer of genes into cells relied upon the non-covalent complexation of the gene with another molecule. The present invention demonstrates that a molecule can be covalently attached to a gene in order to enable its cellular transport and that the gene can still be functional.

The gene is a polynucleotide that expresses a protein from the polynucleotide's coding sequence. In a preferred embodiment, the gene is a double-stranded DNA derived from either plasmid DNA in bacteria or from polymerase chain reaction amplification (PCR). The sequences within the DNA-based gene includes a promoter, enhancer, 5' untranslated regions, 3' untranslated regions, introns, poly A addition site and transcription terminators.

There are a variety of molecules (gene transfer enhancing signals) that can be covalently attached to the gene in order to enable or enhance its cellular transport. These include signals that enhance cellular binding to receptors, cytoplasmic transport to the nucleus and nuclear entry or release from endosomes or other intracellular vesicles.

Nuclear localizing signals enhance the entry of the gene into the nucleus or directs the gene into the proximity of the nucleus. Such nuclear transport signals can be a protein or a peptide such as the SV40 large T ag NLS or the nucleoplasmin NLS.

Other molecules include ligands that bind to cellular receptors on the membrane surface increasing contact of the gene with the cell. These can include targeting group such as agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

These gene transfer enabling molecules (protein, sugars, lipids, polynucleotides) can be covalently attached to the gene by various methods. These include the use of the compounds R Cl (4-(N-2-chloroethyl-N-methylamino)-benzenamine) and its derivatives. It also includes the use of compounds containing the CPI DNA alkylating moiety (cyclopropa-pyrrolo-indol) and its derivatives.

In one preferred embodiment, a gene can be covalently modified outside of the sequences required for expression. Expression means the transcription of the gene into RNA or the translation of RNA into protein. Thereby, the covalent modification outside of the sequences necessary for expression does not prevent the expression of the gene. This can be accomplished by first chemically modifying a piece of DNA that is then ligated to the expression part of the DNA.

In another preferred embodiment, the chemical group can be attached to the sequences necessary for expression but it does not prevent the transcription or translation process.

Provided is a method for enhancing gene delivery to a cell, comprising, covalently attaching a compound to the gene for targeting a location and not preventing gene expression; and, exposing a cell to the gene.

Provided is a method for expressing a gene, comprising, covalently attaching a compound to a gene providing a modified expressible gene for locating a target; and, delivering the modified gene to a cell.

Reference is now made in detail to the preferred embodiments of the invention, examples of which are illustrated in the accompanying drawings.

DETAILED DESCRIPTION

Figure 1A:
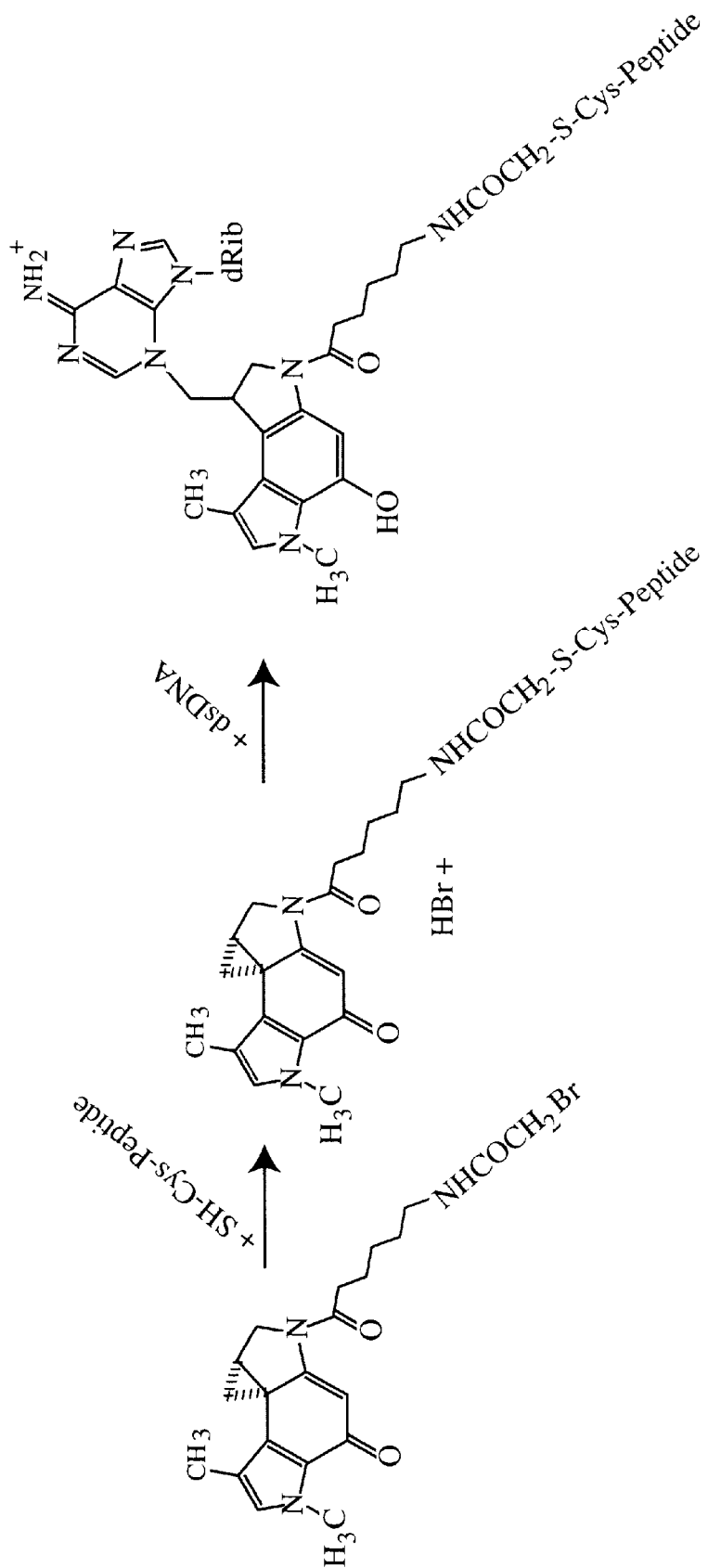
FIGS. 1A–1C illustrate covalent attachment of peptides to double stranded DNA.

The present invention relates to a process of delivering a gene to a cell. Delivering a gene means that the gene is placed in a position to become associated with the cell. The gene can be on the membrane of the cell or inside the cytoplasm, nucleus, or other organelle of the cell. The process of delivering a gene to a cell has also been commonly termed "transfection" or the process of "transfecting" and also it has been termed "transformation." The cell can be a mammalian cell that is within the tissue in situ. The cell can also have been removed and maintained in tissue culture in a primary, secondary, immortalized or transformed state.

The gene, as used in this specification, is a unit of coded information usually used to make a functional product. It is a polynucleotide and can be double-stranded DNA, single-stranded DNA, or a messenger RNA. The double-stranded DNA is typically derived from either plasmid DNA in bacteria or from polymerase chain reaction amplification (PCR). These polynucleotides contain a coding sequence for a polypeptide or protein and the associated sequences required for expression. For the DNA this includes a promoter, enhancer, 5' untranslated regions, 3' untranslated regions, introns, poly A addition site and transcription terminators. For RNA, a promoter, enhancer, poly A addition site, or transcription terminator would not be necessary. An oligonucleotide such as an antisense molecule that doesn't express a protein is excluded from this definition of a gene.

Attachment of A Signal Molecule to A Gene Without Preventing Its Expression

The gene transfer enhancing signal is attached covalently to the gene using a variety of methods. They can be alkylating reagents or photoactivatable compounds. Examples of alkylating reagents include the use of mustards and the use of compounds containing the CPI DNA alkylating moiety (cyclopropa-pyrrolo-indol) and its derivatives. All compounds in the CPI family include the functionality: 1,2,8,8a-tetrahydro-7-methylcyclopropa-[c]pyrrolo-[3,2-e] indol-4(5H)-one.

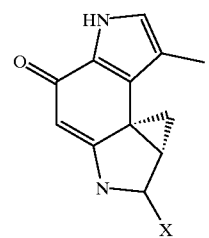

X = any mole

Mustards are molecules consisting of a nucleophile and a leaving group separated by an ethylene bridge. After internal attack of the nucleophile on the carbon bearing the leaving group a strained three membered group is formed. This strained ring (in the case of nitrogen mustards an aziridine ring is formed) is very susceptible to nucleophilic attack. Thus allowing mustards to alkylate weak nucleophiles such as polynucleic acids. Mustards can have one of the ethylene bridged leaving groups attached to the nucleophile, these molecules are sometimes referred to as half-mustards; or they can have two of the ethylene bridged leaving groups attached to the nucleophile, these molecules can be referred to as bis-mustards. One type of mustards are R-chloride derivatives that contain the aromatic nitrogen mustard 4-[(2-chloroethyl)-methylamino]-benzylamine. We incorporate herein by reference a patent application entitled: A Method for Single-Step Attachment of a Label to Target Molecules, Ser. No. 08/982,485 filed Dec. 2, 1997.

A gene can be covalently modified outside of the sequences required for expression. Expression as used in this specification means the transcription of the gene into RNA or the translation of RNA into protein. DNA sequences necessary for expression or transcription include sequences such as promoters, enhancers, 5' untranslated regions, 3' untranslated regions, introns, poly A addition site and transcription terminators. Thereby, the covalent modification outside of the sequences necessary for expression does not prevent the expression of the gene. In one preferred embodiment, this can be accomplished by first chemically modifying a piece of DNA that is then ligated to the expression part of the DNA. Ligation indicates that the modified DNA is attached to the sequence necessary for expression via a phosphodiester bond. Typically, the ligation is enabled by complementary overlapping DNA sequences that are then ligated by an enzyme such as ligase. In addition, the chemically modified DNA may be associated with the expressing DNA fragment via another type of covalent bond such as using alkylating reagents.

In another preferred embodiment, targeted attachment may be accomplished by using a chemical or protein that binds at a specific DNA sequence not required for expression. This protein may be an enzyme that attaches a molecule to the DNA. For example a biotin may be covalently attached to a sequence not necessary for expression. A nucleotide derivative containing a biotin may be enzymatically attached to the DNA. Enzymes that could attach a chemically-modified nucleotide include polymerases such as Klenow and Taq polymerase and terminal transferase. A protein or peptide that binds biotin (e.g. avidin, strepavidin, neutravidin) could bind the biotin and a signal could be attached to the protein that binds biotin.

In addition, the chemical group can be attached to the sequences necessary for expression but it does not prevent the transcription or translation process. For example, small signal molecules may not interfere with expression if they are small enough or are cleaved.

Furthermore, the chemically modified DNA could be associated with the expressing DNA fragment via a strong non-covalent bond(s) such as complementary sequences that hybridize via Watson-Crick bonding without undergoing ligation, sequences that form triple-helix or other type of non-Watson-Crick bonding, and the avidin-biotin system and its derivatives. A biotin derivative is any compound that contains biotin.

Gene Transfer Enhancing Signals

The gene transfer enhancing signal (or abbreviated as the Signal) is defined in this specification as a molecule that modifies the gene and can direct it to a cell location (such as tissue) or location in a cell (such as the nucleus) either in culture or in a whole organism. By modifying the cellular or tissue location of the foreign gene, the expression of the foreign gene can be enhanced.

The gene transfer enhancing signal can be a protein, peptide, lipid, steroid, sugar, carbohydrate, (non-expresssing) polynucleic acid or synthetic compound. The gene transfer enhancing signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS SEQ ID NO: 7/(H-CGYGPKKKRKVGG-OH) or long NLS's SEQ ID NO: 1/(H-CKKKSSSDDEATADSQHSTPPKKKRKVED-PKDFPSELLS-OH and SEQ ID NO: 2/H-CKKKWDDEATADSQHSTPPKKKRKVEDPKDIFPS-ELLS-OH). Other NLS peptides have been derived from M9 protein (CYNDFGNYNNQSSNFGPMKQGNFGGR-SSGPY), EIA SEQ ID NO: 4 (H-CKRGPKRPRP-OH), nucleoplasmin SEQ ID NO: 5/(H-CKKAVKRPAATKKAGQAKKK.L-OH),and c-myc SEQ ID NO: 6/(H-CKKKGPAAKRVKLD-OH).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin Al and the ER-retaining signal (KDEL sequence), viral components such as influenza virus hemagglutinin subunit HA-2 peptides and other types of amphipathic peptides.

Cellular receptor signals are any signal that enhances the association of the gene with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asi-ologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

EXAMPLES

Example 1.

Figure 1B:
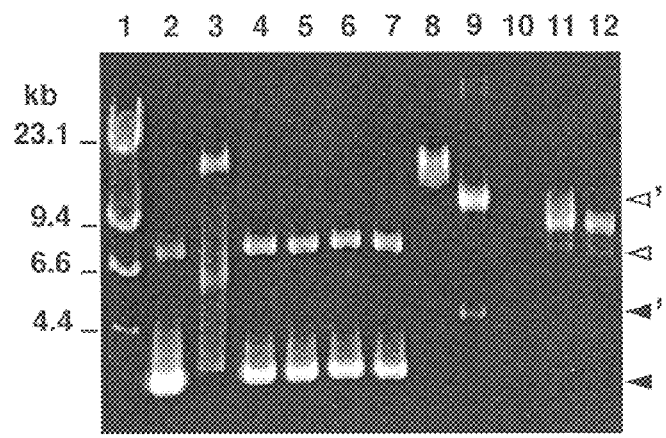

Positively charged peptides can be covalently attached to DNA.
Results:

The SV40 large T antigen NLS peptide was conjugated to a bromoacetamide derivative of CPI [(+)-CPI-BrAc] through the sulfhydryl group of the peptide's N-terminal cysteine residue to form CPI-peptide (FIG. 1A). [A. Chemical structures of the reagents and outline of the conjugation steps.] Agarose gel electrophoresis was performed on a 5.4 kb pDNA following its incubation with either the NLS peptide alone or the CPI-NLS conjugate (FIG. 1B). [B. DNA-peptide interactions analyzed on a 0.7% agarose gel. The untreated 5.4 kb pDNA (lane 2) was mixed and incubated with either free NLS peptide (lane 3) or with CPI-NLS conjugate (lane 8) at a 0.5:1 peptide to DNA weight ratio. After this incubation, and after each subsequent steps of the protocol, aliquots containing an estimated 300 ng DNA were saved for loading into the designated lane of the gel, and the rest of the reaction was used for the next treatment. Samples were washed with 1M NaCl (lanes 4 and 9). Half of both samples were phenol extracted and the aqueous phase collected (lanes 5 and 10). The other halves were proteinase-K treated with 100 $\mu$g/ml enzyme at 55° C. for 1 hr (lanes 6 and 11), and were phenol extracted following the proteinase-K digestion (lanes 7 and 12). Closed arrows point at the supercoiled, open arrows point at the open circular form of the pDNA. The arrows for the NLS-modified supercoiled and relaxed forms are marked with an apostrophe. Molecular size ladder: HindIII digested $\lambda$ phage DNA (lane 1).] The presence of the peptide altered the mobility of the pDNA in both cases (FIG. 1B, lanes 3 and 8). However, after removing the non-covalently bound peptide by 1 M NaCl washes, the migration of pDNA incubated with CPI-NLS remained retarded (FIG. 1B, lane 9), while migration of pDNA incubated with NLS alone was similar to the untreated pDNA (FIG. 1B, lane 4). Also, the majority of the supercoiled DNA became nicked after the alkylation step. The pDNA incubated with CPI-NLS could not be recovered in the aqueous phase after phenol extraction (FIG. 1B, lane 10), while pDNA incubated with NLS alone remained in the aqueous phase (FIG. 1B, lane 5). The CPI-NLS treated DNA formed a visible layer on the interphase from where it could be recovered by adding 0.1 M HEPES (pH 7.2) and removing the phenol by three extraction steps with HEPES buffer saturated normal butanol. Proteinase-K digestion of the pDNA/CPI-NLS complex decreased the gel retardation (FIG. 1B, lane 11) and the treated DNA remained in the aqueous phase after phenol extraction (FIG. 1B, lane 12). The same protease treatment had no effect on the pDNA mixed with NLS alone (FIG. 1B, lanes 6–7). These results suggested that the NLS peptide was covalently linked to the pDNA, presumably as a N3 adenine adduct (FIG. 1A).

Further confirmation of covalent linkage was obtained by monitoring the characteristic absorption of the cyclopropapyrroloindole ring-system at 355 nm. Reaction of the CPI with DNA leads to the loss of the cyclopropyl ring and a decrease in absorption at 355 nm (Lukhtanov, E. A., Podyminogin, M. A., Kutyavin, I. V., Meyer, R. B. and Gamper, H. B. 1996. Rapid and efficient hybridization-triggered crosslinking within a DNA duplex by an oligodeoxyribonucleotide bearing a conjugated cyclopropapyrroloindole. *Nucl. Acids Res.* 24:683–687.). For 20 µg pDNA and 10 µg CPI-NLS in 400 µl reaction volume, the $\Delta Abs_{355}$ value after 12 minutes of incubation indicated the loss of 2.7 µM cyclopropyl ring of the 24 µM total. The control reaction containing the same amount of pDNA and CPI showed a decrease of only 0.2 µM. The difference between the CPI and CPI-NLS samples gradually increased over time, reaching 6.4 µM (27% of initial amount of CPI) by the end of the 60 minute incubation at 37° C. When reactions at the same CPI-NLS to DNA ratio were supplemented with 20 mM, 100 mM or 150 mM NaCl, the $\Delta Abs_{355}$ values showed only 5.7, 1.0 and 0.3 µM peptide-dependent decreases, respectively. After removing the unbound peptide by 1M NaCl washes, the samples were analyzed by gel electrophoresis. They showed retardation positively correlated with their $\Delta Abs_{355}$ values (FIG. 1C, lanes 2–5) [C. Agarose gel (0.7%) electrophoresis of a 5.4 kb plasmid DNA (lanes 1 and 6) conjugated to CPI-NLS at 0.5:1 peptide to DNA weight ratio in the presence of NaCl concentrations of 0 mM (lane 2), 20 mM (lane 3), 100 mM (lane 4) or 150 mM (lane 5). $\Delta Abs_{355}$ values during the above conjugations were 6.4, 5.7 1.0 and 0.3 µM, respectively. Samples containing an estimated 300 ng DNA were loaded following 1 M NaCl washes. Arrows and ladder (lane 7) are as in panel B.] These results indicate that the reaction of CPI with DNA is greatly enhanced when CPI is linked to the DNA-binding cationic NLS peptide, provided that the salt concentration is sufficiently low to allow for electrostatic interactions.

Measuring the decrease of $Abs_{355}$ also provides a method to approximate the average number of NLS peptides that are attached to the pDNA. For example, in the above reaction of 20 µg pDNA with 10 µg CPI-NLS in 400 µl buffer, the loss of 6.4 µM cyclopropyl ring suggests that about 460 molecules of NLS peptide were conjugated to each 5.4 kb pDNA; that is 85 peptides per 1 kb. Quantitative data obtained by measuring $\Delta Abs_{355}$ were in agreement with the number of attached peptides determined using the ATTO-TAG CBQCA protein quantitation kit.

Methods:
Preparation of fluorescently labeled DNA—Primary amine groups were introduced into double stranded DNA by two alternative approaches. 4-(N-2-chloroethyl-N-methylamino)-benzylamine RCl) (kindly provided by A. Mustaev) alkylates guanines at the N7 ring nitrogen (Grineva, N., Knorre, D. and Kurbatov, V. 1971. Highly efficient alkylation of transport RNA by 4-(N-2-chloroethyl-N-methylamino)benzylamine. *Doklady Akademii Nauk SSSR* 201:609–611.). It was dissolved in dimethylformamide (DMF) and mixed with double stranded DNA (2 µg/µl final concentration) at 1:6 RCl to nucleotide molar ratio, in PBS containing 25% DMF. Reactions were incubated overnight at room temperature (RT) followed by gel filtration on Sephadex G-25 (NAP-5 columns; Pharmacia). The amine-modified DNA was concentrated in an Ultrafree-MC 30,000 NMWL ultrafiltration unit (Millipore). Another approach involved the use of 4-(phenyl-azido-salicyl-amido)-butylamine (ASBA) (Pierce) which reacts with nucleophilic groups of the DNA after photoactivation. ASBA was dissolved in PBS and added to the DNA (1.2 µg/µl final DNA concentration) at a molar ratio of 1.3:1 ASBA to nucleotide. The samples were UV illuminated as previously described (Dowty, M. E., Guervich, V., Berg, R. K., Repetto, G. and Wolff, J. A. 1992. Characterization of biotinylated and gold labeled plasmid DNA. *Meth. Molec. Cell. Biol.* 3:167–174.). Excess ASBA was removed and the DNA was concentrated as above.

Amine-modified DNA samples were then conjugated either to tetramethyl-rhodamine-5-isothiocyanate (TRITC; Sigma) or to Cy5-N-hydroxysuccinimidyl ester (FluoroLink; Biological Detection Systems). TRITC was conjugated in 100 mM $NaHCO_3$ pH 9.2 at 1:6 TRITC to nucleotide molar ratio (1.2 µg/µl final DNA concentration) during an incubation period of 4 hours at RT. The product was purified by gel filtration (NAP-5 column; Pharmacia) and then exhaustively washed with 100 mM HEPES pH 7.2 in an Ultrafree-MC 30,000 NMWL ultrafiltration unit (Millipore) in order to remove any traces of unbound rhodamine. Cy5 conjugation was performed as described for TRITC, except for the addition of 200 mM NaCl to prevent electrostatic repulsion between the negatively charged Cy5 reagent and the DNA.

The number of fluorochromes attached to the DNA was determined using a Hitachi F-3010 Fluorescence Spectrophotometer. Fluorescence of tetramethyl-rhodamine or Cy5 was measured at 541 nm excitation and 572 nm emission, or at 650 nm excitation and 667 nm emission wavelength, respectively. Calibration curves were taken using free TRITC and Cy5-dCTP (DuPont NEN). Different batches of labeled DNA were found to carry 5–12 fluorochrome molecule/1 kb.

Covalent attachment of peptides to DNA: The (+)-2-(N-bromoacetyl-6-aminohexanoyl)-1,2,8,8a -tetrahydro-5,7-dimethylcyclopropa[c]pyrrolo[3,2-e]indol-4(5H)-one [(+)-CPI-BrAc] has been synthesized. Sequence and structure dependence of the hybridization-triggered reaction of oligonucleotides bearing conjugated cyclopropapyrroloindole. *J. Am. Chem. Soc.* ).The following peptides were synthesized by Research Genetics (Huntsville, Ala.): wild type SV40 large T antigen NLS (NLS) CGYGPKKKRKVGG; D-stereoisomer SV40 NLS (DNLS) SEQ ID NO: 8/DCGDYGDPDKDKDKDRDKDVGG; mutant SV40 NLS (mNLS) SEQ ID NO: 9/CGYGPKDKRKVGG (the $Lys^{128}$ mutant, known to be transport deficient) (Kalderon, D., Roberts, B. L., Richardson, W. D. and Smith, A. E. 1984. A short amino acid sequence able to specify nuclear location. *Cell* 39:499–509.); randomized SV40 NLS (rNLS) SEQ ID NO: 10/CGKGKPRKVKYGW; oligo-lysine (oligoK) CKKWKKKG SEQ ID NO: 11. CPI was dissolved in DMF and added to the peptides (2–3 µg/µl final concentration) at a 1.2-fold molar excess in 50 mM $Na_2HPO_4$ pH 8.0 containing 25% final DMF. Reactions were incubated at RT for 2 hours. Then the CPI-peptide conjugates were mixed with circular or linear, fluorochrome labeled or unlabeled double stranded DNA of various sizes and origins. The final DNA concentration in the reactions was 0.05–0.2 µg/µl. In order to avoid precipitation of the DNA, the peptide was added at various, but always lower than charge-neutralizing ratios (<0.9:1 ratio of positive:negative charge, except for MnNLS which did not precipitate the DNA even at ratio of 1.4:1). The alkylation reaction occurred in 100 mM HEPES pH 7.2 at 37° C. for 1 hr. The unreacted CPI-BrAc and CPI-peptide conjugate was removed by washing the samples twice with 1 M NaCl in Ultrafree-MC 30,000 NMWL ultrafiltration units (Millipore), followed by three more washes with the buffer used in the subsequent step. Peptide conjugated DNA samples were analyzed for altered mobility on 0.5 or 0.7% agarose gels. The gels were stained with ethidium bromide after electrophoresis.

During the 1 hr CPI alkylation reaction, the $Abs_{355}$ of the cyclopropyl moiety was measured at different time-points in a quartz micro-cuvette using a 9420 UV-Visible Spectrophotometer (IBM Instruments). The frequency of alkylation, expressed as the number of attached peptides per 1 kb DNA, was calculated based on a calibration curve of intact CPI-BrAc and the amount of DNA added to the reaction (1 µg dsDNA=$1.5 \times 10^{-12}$ mole 1 kb fragment). Data obtained by the above method were confirmed by determining the number of primary amine groups on known quantities of conjugated DNA using the ATTO-TAG CBQCA protein quantitation kit (Molecular Probes). The kit was used according to the manufacturer's protocol. The unconjugated peptide in a range of 0.1–1.5 nmole amount of primary amine groups was used for the calibration curve.

Results:

The SV40 large T antigen NLS peptide was conjugated to a bromoacetamide derivative of CPI [(+)-CPI-BrAc] through the sulfhydryl group of the peptide's N-terminal cysteine residue to form CPI-peptide (FIG. 1A). Agarose gel electrophoresis was performed on a 5.4 kb pDNA following its incubation with either the NLS peptide alone or the CPI-NLS conjugate (FIG. 1B). The presence of the peptide altered the mobility of the pDNA in both cases (FIG. 1B, lanes 3 and 8). However, after removing the non-covalently bound peptide by 1 M NaCl washes, the migration of pDNA incubated with CPI-NLS remained retarded (FIG. 1B, lane 9), while migration of pDNA incubated with NLS alone was similar to the untreated pDNA (FIG. 1B, lane 4). Also, the majority of the supercoiled DNA became nicked after the alkylation step. The pDNA incubated with CPI-NLS could not be recovered in the aqueous phase after phenol extraction (FIG. 1B, lane 10), while pDNA incubated with NLS alone remained in the aqueous phase (FIG. 1B, lane 5). The CPI-NLS treated DNA formed a visible layer on the interphase from where it could be recovered by adding 0.1 M HEPES (pH 7.2) and removing the phenol by three extraction steps with HEPES buffer saturated normal butanol. Proteinase-K digestion of the pDNA/CPI-NLS complex decreased the gel retardation (FIG. 1B, lane 11) and the treated DNA remained in the aqueous phase after phenol extraction (FIG. 1B, lane 12). The same protease treatment had no effect on the pDNA mixed with NLS alone (FIG. 1B, lanes 6–7). These results suggested that the NLS peptide was covalently linked to the pDNA, presumably as a N3 adenine adduct (FIG. 1A).

Further confirmation of covalent linkage was obtained by monitoring the characteristic absorption of the cyclopropapyrroloindole ring-system at 355 nm. Reaction of the CPI with DNA leads to the loss of the cyclopropyl ring and a decrease in absorption at 355 nm (Lukhtanov, E. A., Podyminogin, M. A., Kutyavin, I. V., Meyer, R. B. and Gamper, H. B. 1996. Rapid and efficient hybridization-triggered crosslinking within a DNA duplex by an oligodeoxyribonucleotide bearing a conjugated cyclopropapyrroloindole. *Nucl. Acids Res.* 24:683–687.). For 20 µg pDNA and 10 µg CPI-NLS in 400 µl reaction volume, the $\Delta Abs_{355}$ value after 12 minutes of incubation indicated the loss of 2.7 µM cyclopropyl ring of the 24 µM total. The control reaction containing the same amount of pDNA and CPI showed a decrease of only 0.2 µM. The difference between the CPI and CPI-NLS samples gradually increased over time, reaching 6.4 µM (27% of initial amount of CPI) by the end of the 60 minute incubation at 37° C. When reactions at the same CPI-NLS to DNA ratio were supplemented with 20 mM, 100 mM or 150 mM NaCl, the $\Delta Abs_{355}$ values showed only 5.7, 1.0 and 0.3 µM peptide-dependent decreases, respectively.

After removing the unbound peptide by 1M NaCl washes, the samples were analyzed by gel electrophoresis. They showed retardation positively correlated with their $\Delta Abs_{355}$ values (FIG. 1C, lanes 2–5) These results indicate that the reaction of CPI with DNA is greatly enhanced when CPI is linked to the DNA-binding cationic NLS peptide, provided that the salt concentration is sufficiently low to allow for electrostatic interactions.

Measuring the decrease of Abs355 also provides a method to approximate the average number of NLS peptides that are attached to the pDNA. For example, in the above reaction of 20 µg pDNA with 10 µg CPI-NLS in 400 µl buffer, the loss of 6.4 µM cyclopropyl ring suggests that about 460 molecules of NLS peptide were conjugated to each 5.4 kb pDNA; that is 85 peptides per 1 kb. Quantitative data obtained by measuring $\Delta Abs_{355}$ were in agreement with the number of attached peptides determined using the ATTO-TAG CBQCA protein quantitation kit.

Figure 1C:
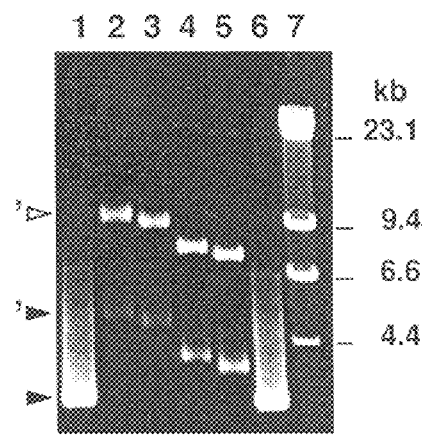

Conclusions:

CPI was linked to a cationic peptide which enabled it to alkylate double stranded DNA. The fact that increased salt concentrations reduced the efficiency of the reaction supports the importance of the ionic interaction between the positively-charged peptides and negatively-charged DNA (FIG. 1C). The cross-linker CPI itself contains sufficient structural information to determine the specific N3 alkylation of adenines (Hurley, L. H., Lee, C. S., McGovren, J. P., Warpehoski, M. A., Mitchell, M. A., et al. 1988. Molecular basis for sequence-specific DNA alkylation by CC-1065. *Biochem.* 27:3886–3892.) (FIG. 1A).

Example 2

Nuclear accumulation of the SV40 NLS-peptide conjugated DNA.

Methods:

HeLa (human epitheloid), COS7 (monkey kidney), C2C12 (mouse muscle), NIH-3T3 (mouse fibroblast), HepG2 (human hepatocellular carcinoma) and SMHEC (mouse heart endothelial) cell lines were grown in Dulbecco's Modified Eagle's Medium (Gibco Laboratories, Gaithersburg, Md.) containing 10% fetal calf serum (Hyclone Laboratories, Logan, Utah) in a humidified incubator at 37° C. with 5% $CO_2$ atmosphere.

The digitonin permeabilized cell assays were performed as previously described (Hagstrom, J. E., Ludtke, J. J., Bassik, M. C., Sebestyen, M. G., Adam, S. A., et al.). Nuclear import of DNA in digitonin-permeabilized cells. *J. Cell Sci.* and Adam, S. A., Sterne-Marr, R. and Gerace, L. 1992. Nuclear protein import using digitonin-permeabilized cells. *Meth. Enzymol.* 219:97–111.). The protocols for inhibition by WGA, NEM, cold and ATP depletion, the method of microinjections and the conditions for confocal and epifluorescent microscopy and image analysis have also been described.

The quantitative effect of the number of conjugated NLS peptides per 1 kb DNA on the efficiency of nuclear uptake was assessed on confocal images. The background value was determined for each image by placing a circle of constant size (1004 pixels) outside of cells and calculating the average brightness of pixels. That was used as a threshold value and was deducted from the whole image. The same circle was then placed in the central area of the nuclei in central optical sections and the number of pixels above the threshold was counted. The data for at least 12 nuclei in each condition are presented.

Figure 2A:
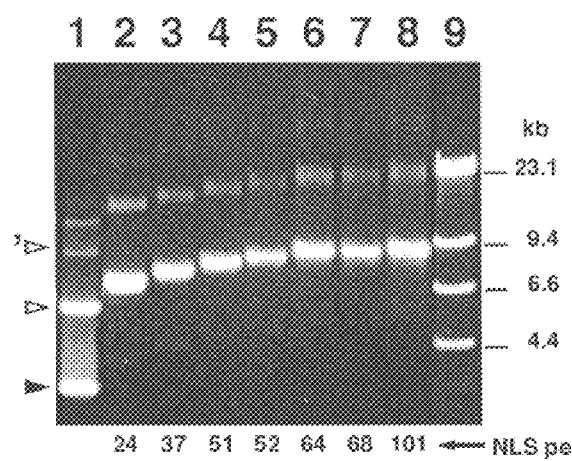
FIGS. 2A–2E illustrate the effect of covalently attached NLS-peptides on the nuclear transport of pDNA at different modification levels.
Figure 2B:
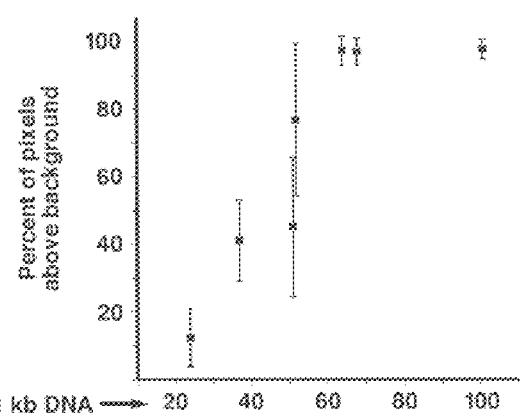
Figure 2C:
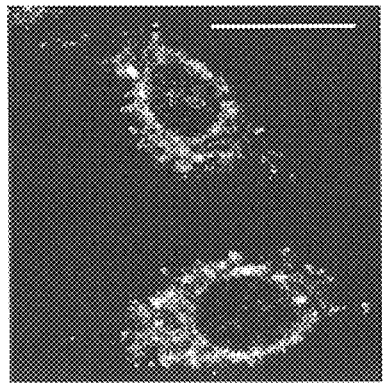
Figure 2D:
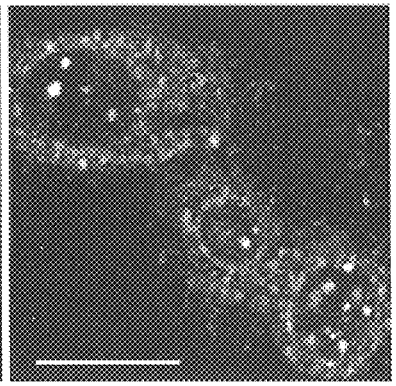
Figure 2E:
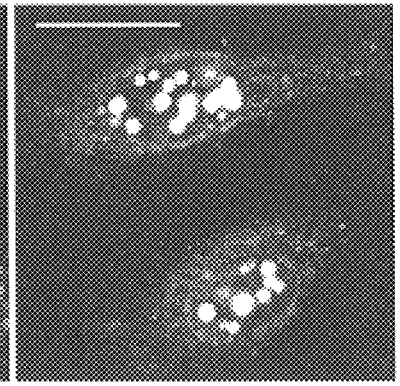

Results:

A 4.8 kb rhodamine labeled pDNA (Rh-pDNA) was conjugated to CPI-NLS at peptide:DNA weight ratios between 0.18:1 and 0.67:1. The extent of gel retardation of 1M salt washed samples was greater with increased peptide:DNA ratios (FIG. 2A). [A. Agarose gel electrophoresis (0.5%) using a 4.8 kb Rh-pDNA (lane 1) conjugated to CPI-NLS peptides at 0.18:1 (lane 2), 0.25:1 (lane 3), 0.33:1 (lane 4), 0.42:1 (lane 5), 0.5:1 (lane 6), 0.58:1 (lane 7) and 0.67:1 (lane 8) peptide to DNA weight ratios. The level of modification (based on $\Delta Abs_{355}$) at each ratio is marked by the number of NLS peptides/1 kb DNA values under the lane. Molecular size ladder: HindIII digested λ phage DNA (lane 9).] The extent of modification was quantitated by measuring the $\Delta Abs_{355}$ values and the approximate numbers of peptides/1 kb were found to vary between 24 and 101 (FIG. 2A). Equal amounts of the above NLS-Rh-pDNA samples and the unconjugated Rh-pDNA control were tested for nuclear import in digitonin permeabilized HeLa cells. The Rh-pDNA (FIG. 4A) [Confocal images of central optical sections of digitonin permeabilized HeLa cells incubated with approximately 200 ng Rh-pDNA without NLS conjugation (A) or NLS-Rh-pDNA (conjugated at 0.63:1 peptide:DNA weight ratio) (B-I) for 1 hour at 37° C. All assays were performed in the presence of RRL, except for B. The nuclear transport was assessed without any additions (C) or with 1 mg/ml WGA (D), 5 mM NEM pre-treatment (E), energy depletion using apyrase and no ATP (F), 30-fold molar excess of pDNA (G), unlabeled NLS-pDNA containing a 30-fold molar excess of NLS peptide as compared to the amount of NLS on the NLS-Rh-pDNA (H) or NLS-Streptavidin containing a 30-fold excess of NLS as in H(I). Scale bars: 20 μm.] and the NLS-Rh-pDNA at the lowest modification level (FIG. 2C) did not accumulate in the nucleus. The NLS-Rh-pDNA samples modified to a higher extent produced punctate nuclear staining (FIG. 2D and 2E). The fluorescent spots did not co-localize with the nucleoli observed on phase contrast images. The intensity of the nuclear accumulation depended on the level of modification, judged both visually (FIG. 2D and 2E) and by measuring the number of pixels brighter than the background in central optical sections of nuclei on confocal images (FIG. 2B). [B. Nuclear fluorescence is depicted by the average percent of pixels brighter than the background in central optical sections. Error bars indicate the standard deviation. Digitonin permeabilized cells were exposed to the above NLS-Rh-DNA samples carrying different number of peptide/1 kb segment, in RRL for 1 hr at 37° C. C-E. Confocal images of central optical sections from representative cells exposed to Rh-DNA that is less modified (24 peptides/1 kb) (C), moderately modified (51 peptides/1 kb) (D), or highly modified (101 peptides/1 kb) E). Scale bars: 20 μm.] The high standard deviations of samples in the middle of the curve are the result of the punctate staining pattern. On images of the highly modified pDNA samples almost all the pixels are brighter than the background (resulting in lower standard deviations) due to the larger and more numerous spots and some weak haze in between them. Based on the conjugation results and microscopic images, there seems to be a threshold for efficient nuclear uptake. NLS-pDNA conjugates bearing less than approximately 40 NLS-peptides/1 kb do not accumulate in the nucleus to a recognizable degree. Above this level of modification, the intensity of transport gradually increases with the number of attached peptides reaching a plateau at about 60 NLS-peptides/1 kb.

Nuclear import assays performed on five other cell lines of different tissue origin (COS7, C2C12, HepG2, NIH-3T3 and SMHEC) resulted in punctate nuclear staining similar to that shown in HeLa cells. Linear and circular DNA samples of various origins and sizes (from 2.7 kb up to 11.1 kb) gave the same staining pattern, although the intensity of nuclear transport diminished with increasing size of the DNA. This suggests that the nuclear uptake of the NLS-modified DNA is independent of cell type, DNA sequence, and is operational in a broad size-range.

Figure 3A:
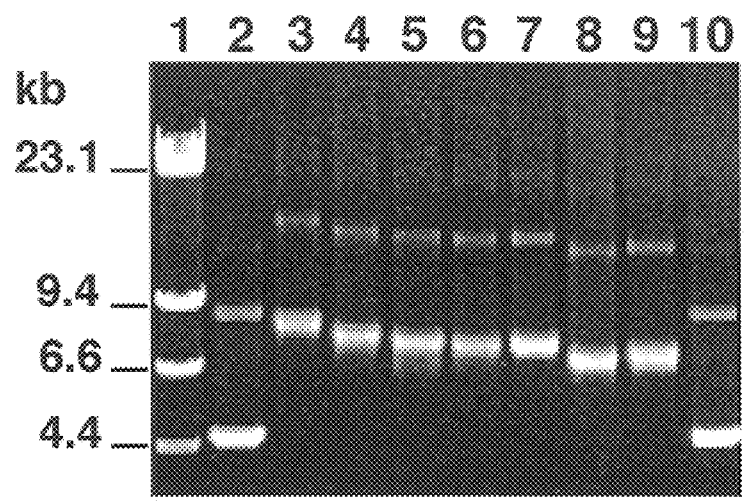
FIGS. 3A–3D illustrate in vitro nuclear import of fluorescent plasmid DNA conjugated to different peptides.

For control purposes, four other peptides that are not NLS's but carry positively charged residues were also conjugated to a 4.8 kb Cy5-labeled pDNA (Cy5-pDNA). Three of the peptides did not carry a known nuclear localization signal (mNLS, rNLS and oligoK). The fourth one had the sequence of the SV40 NLS-peptide, but was synthesized using the D-stereoisomers of the amino acids (DNLS). Since the mNLS peptide has only three positive charges, while the other peptides have five, it could be used at higher peptide to DNA ratios without precipitating the DNA. At identical ratios it induced allylation much less efficiently than peptides with five net positive charges. As none of the peptides were reduced by a reducing agent prior to conjugation, the varying degree of the CPI-peptide coupling could result in some variability in the efficiency of the DNA alkylation step, independently of the nominal peptide:DNA ratio. Nevertheless, all four peptides were conjugated, as judged by their gel shift, to the pDNA at comparable or higher modification levels than obtained with the wild type NLS peptide (FIG. 3A). [A. Agarose gel electrophoresis (0.5 %) of a 4.8 kb Cy5-pDNA that is unmodified (lanes 2 and 10), conjugated to CPI-NLS at peptide to DNA ratios of 0.75:1 (lane 3), 0.55:1 (lane 6) or 0.4:1 (lane 9), or conjugated to CPI-DNLS at 0.8:1 (lane 4), CPI-oligoK at 0.6:1 (lane 5), CPI-mNLS at 2:1 (lane 7) or CPI-rNLS at 0.6:1 weight ratios (lane 8). Molecular size ladder: HindIII digested λ phage DNA (lane 1).] Equal amounts of these conjugates were tested for nuclear transport in digitonin treated cells. The wild type NLS-Cy5-pDNA showed punctate nuclear staining (FIG. 3B), [B-D. Epifluorescent microscopic images of digitonin treated HeLa cells exposed for 1 hour at 37° C. in the presence of cytosolic extract to approximately 300 ng of the following Cy5-pDNA conjugated as in (A) with NLS (from lane 6) (B), DNLS (C), or mNLS (D). Scale bars: 20 μm.] even when using the least modified sample (FIG. 3A, lane 9). All the others were excluded from the nuclei (DNLS-Cy5-pDNA and mNLS-Cy5-pDNA shown on FIG. 3C and 3D, respectively), showing a staining pattern similar to the unconjugated DNA (FIG. 4A). These results indicate that nuclear entry requires the use of a NLS.

Conclusions:

A significant increase in the nuclear uptake of pDNA in an in vitro import assay was induced by its covalent modification with the SV40 NLS peptide (FIG. 2E).

Example 3

Nuclear transport is not the result of selective degradation or conformational changes in the DNA.

Methods:

Electron microscopic examination of unmodified DNA, Rh-DNA, and NLS-Rh-DNA was performed using two independent techniques. Samples were diluted to 20 ng/ml in 2 mM EDTA. 1 μl aliquots were used for the preparation of cytochrome c spreads by the droplet microdiffusion technique, and for adsorption to freshly cleaved mica, both as described (Spiess, E. and Lurz, R. 1988. Electron microscopic analysis of nucleic acids and nucleic acid-protein complexes. *Meth. Microbiol.* 20:293–323.). Specimens were analyzed with a Hitachi H-600 electron microscope at the Medical School Electron Microscope Facility, University of Wisconsin-Madison.

Light scattering determinations were done on 500 μl aliquots of a 8 ng/μl pDNA solution (in 20 mM HEPES buffer, pH 7.2) mixed with equal volumes of buffer containing 0.0–4.8 μg NLS-H1 protein (Fritz, F. D., Herweijer, H., Zhang, G. and Wolff, J. A. 1996. Gene transfer into mammalian cells using histone-condensed plasmid DNA. *Hum. Gene Ther.* 7:1395–1404.) or 0.0–3.2 μg free or CPI conjugated SV40 NLS peptide. The above range represented 0–96% charge neutralization ratios in 16% increments. The mixtures were incubated on ice overnight. The formation of aggregates was detected by measuring light scattering in a Hitachi F-3010 Fluorescence Spectrophotometer, using 400 nm excitation and 400 nm emission wavelength.

200 ng DNA was digested with 0.7, 0.3 and 0.15 units of DNase I (Worthington Biochemical) in 50 mM Tris/HCl pH 7.5, 10 mM $MgCl_2$, 50 mg/ml BSA for 30 min at 37° C., in 15 μl final volume. In order to ensure equal incubation times the enzyme was added last, on the wall of each 1.5 ml tube in 1 μl volume. Samples were briefly spun before transferring them to 37° C. for 30 min. Reactions were stopped by quickly chilling all the tubes on ice and by the addition of 3 μl 6x gel loading buffer type m (Sambrook, J., Fritsch, E. and Maniatis, T. 1989. *Molecular cloning: a laboratory manual*. Cold Spring Harbor Laboratory Press, New York.), containing 10 mM EDTA. The treated samples were analyzed on 1% agarose gel.

Results:

Increased DNase sensitivity leads to smaller DNA fragments that better accumulate in the nucleus. To test this, the DNase sensitivities of NLS-pDNA samples modified to different extents were compared to the sensitivity of unmodified pDNA by digesting equal amounts with serial dilutions of DNase I. All samples were completely digested with a sufficient amount of enzyme, but the NLS-pDNA seemed to be moderately protected at low enzyme concentrations, rather than being more sensitive. Thus, a higher degree of enzymatic degradation of the NLS-pDNA in the assay system is unlikely to be responsible for the selective nuclear accumulation of NLS (and only the wild type NLS) modified pDNA. To examine how stable the DNA samples were in the rabbit reticulocyte lysate (RRL, a potential source of cellular DNase), aliquots were analyzed by gel electrophoresis after a 1 hour incubation at 37° C. Unconjugated Rh-pDNA, transporting NLS-Rh-pDNA, and non-transporting conjugates carrying the randomized or mutant NLS-peptides all appeared equally intact.

DNA alkylated by CC-1065 or its derivatives has been reported to suffer strand breakage at the adduct sites at extreme temperatures (95–100° C.) (Sun, D. and Hurley, L. H. 1992. Effect of the (+)-CC-1065-(N3-adenine)DNA adduct on in vitro DNA synthesis mediated by Escherichia coli DNA polymerase. *Biochem.* 31:2822–2829.). The stability of a DNA sample highly modified by CPI-peptides was studied at different pH values and temperatures. No chemical fragmentation could be observed between pH 6–8, and between temperatures 4–37° C., after an overnight incubation. However, DNA samples alkylated both by the RCl-fluorochrome adduct and by the CPI-peptides, showed the signs of fragmentation on agarose gels after an overnight incubation at 37° C. The conditions of the import assay (1 hour at 37° C. and neutral pH) had no harmful effect, though, on any of our conjugates. Thus, nuclear import due to chemical instability, resulting in small peptide-bearing fragments, is not likely.

Since DNA aggregation typically occurs when DNA (at the concentrations used in this study) is condensed, light scattering measurements were also performed to detect the aggregation of pDNA mixed with a well known DNA condensing agent (histone HI), with NLS peptide (unable to covalently attach to DNA) or with CPI-NLS peptide conjugate. While the positive control, histone H1, was able to substantially increase light scattering, the peptide or the CPI-NLS conjugate caused very little increase in light intensity at the highest modification level (100 peptides/1 kb DNA) which corresponds to approximately 25% charge neutralization. This lack of aggregation is consistent with the electron microscopic images.

Conclusions:

These results demonstrate that the covalent modification does not dramatically alter the physical structure of the gene. This is in sharp contrast to the non-covalent binding of polycations such as polylysine which condenses or aggregates the DNA.

Example 4

The pathway of nuclear translocation.

Methods:

The SV40 large T antigen NLS peptide was cross-linked to allophycocyanin (APC) (Calbiochem) and streptavidin (StAv) (Sigma) in a 20-fold molar excess using the heterobifunctional crosslinker sulfo-SMCC (Pierce) as described (Adam, S. A., Sterne-Marr, R. and Gerace, L. 1992. Nuclear protein import using digitonin-permeabilized cells. *Meth. Enzymol.* 219:97–111.). APC is naturally fluorescent (excitation maximum at 650 nm, emission maximum at 660 nm). The NLS-StAv was labeled by mixing it with 100-fold molar excess of fluorescein-biotin (Sigma), and removing the unbound fluorescein-biotin by excessive washing in an Ultrafree-MC 30,000 NMWL ultrafiltration unit (Millipore).

Figure 3B:
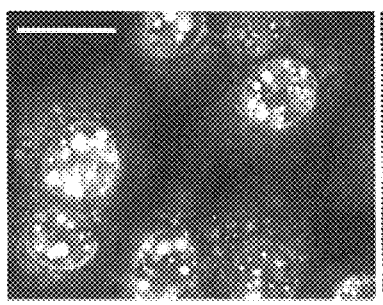
Figure 3C:
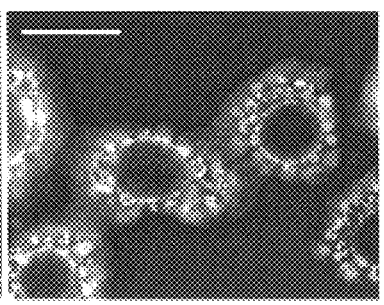
Figure 3D:
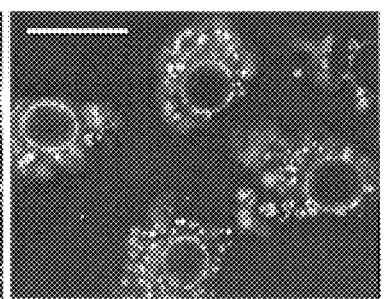
Figure 4A:
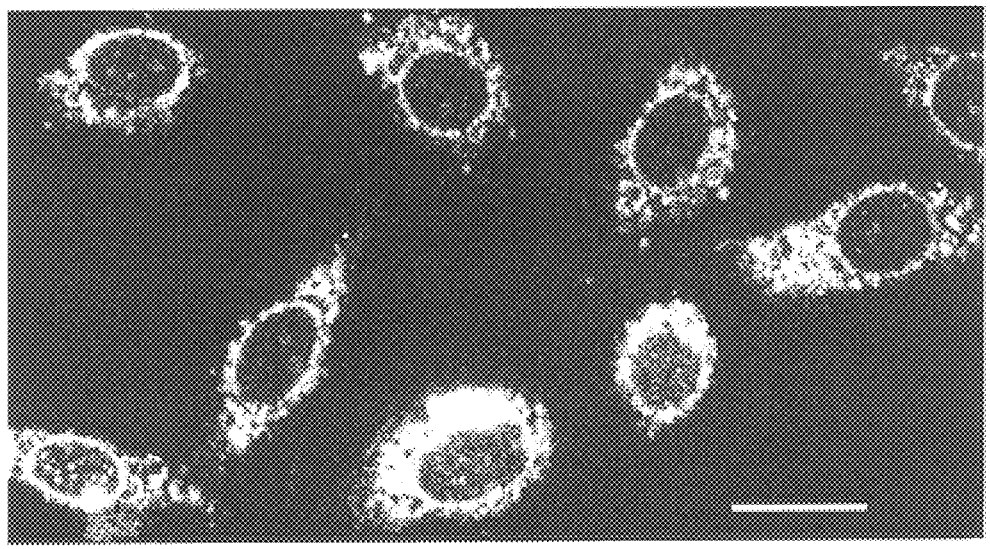
FIGS. 4A–4B illustrate inhibition assays revealing the pathway of transport.
Figure 4B:
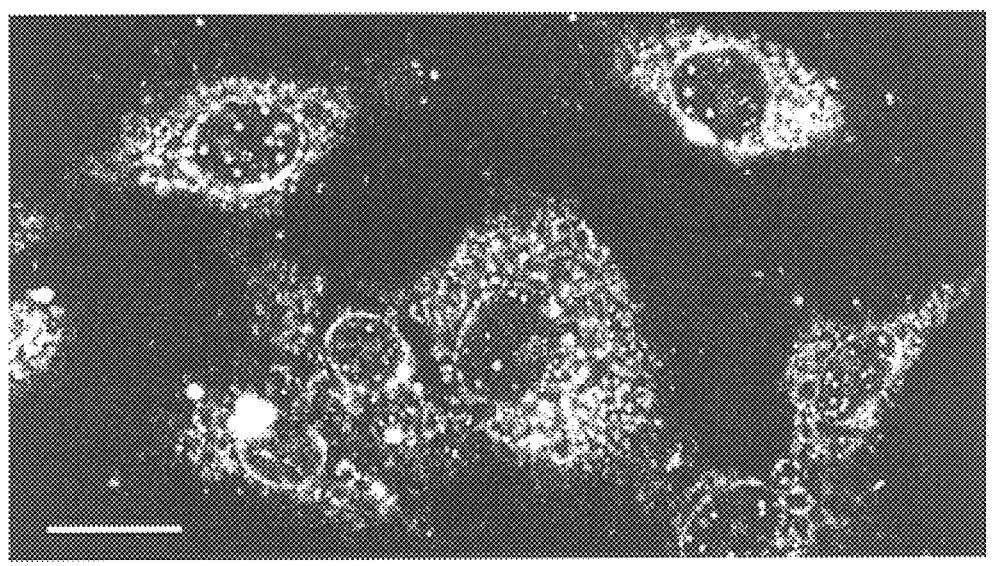

Results:

Whereas unconjugated Rh-pDNA failed to enter the nuclei of digitonin permeabilized cells (FIG. 4A), conjugates carrying a high number of SV40 NLS-peptides accumulated in the nuclei as bright spots (FIG. 2E, 3B and 4C.). No transport of the NLS-Rh-pDNA was observed in the absence of RRL (FIG. 4B), suggesting that its import is dependent on soluble cytoplasmic factors.

The route and mechanism of nuclear import of NLS-Rh-pDNA were investigated by inhibition assays. The transport was strongly inhibited in the presence of the lectin WGA (FIG. 4D), which is known to inhibit NLS-protein import through the nuclear pore (Adam, S. A., Marr, R. S. and Gerace, L. 1990. Nuclear protein import in permeabilized mammalian cells requires soluble cytoplasmic factors. *J. Cell Biol.* 111:807–816.). The pre-treatment of the cells with NEM, which alkylates sulfhydryl groups on proteins essential for the transport of karyophilic proteins and naked DNA, also blocked nuclear staining (FIG. 4E). Incubation at 4° C. or the omission of ATP and addition of apyrase to deplete the cells of energy (FIG. 4F) gave similar inhibitory results. These data indicate an energy dependent active transport through the nuclear pore complex. Excess pDNA (FIG. 4G), RNA, or oligonucleotides did not affect the nuclear accumulation of the NLS-Rh-DNA. However, when the NLS-Rh-DNA was mixed with a 30-fold molar excess of NLS carried either by unlabeled NLS-pDNA (FIG. 4H) or NLS-Streptavidin (NLS-StAv, FIG. 4I), the nuclear staining was significantly reduced. When in the reciprocal experiment the NLS-StAv-Fluorescein-Biotin complex was mixed with either excess unlabeled NLS-pDNA or NLS-StAv, they decreased the nuclear accumulation of the transport substrate. Neither the NLS-Rh-pDNA nor the NLS-protein transport was inhibited by excess unattached NLS-peptide. Based on these data it seems that the NLS-conjugated pDNA is transported through the nuclear pore by the same saturable pathway which is used for the nuclear import of NLS-containing karyophilic proteins.

Conclusions:

These results suggest that the NLS peptide enhanced the nuclear uptake of pDNA via the classical pathway for the nuclear transport of karyophilic proteins. This provides definitive evidence that the covalently attached peptide is functioning as a NLS and a gene transfer enhancing signal.

Example 5

Gene expression from NLS conjugated DNA

Methods:

Ligation of naked DNA to peptide-conjugated DNA—The pBS.CMVLux (6.1 kb) vector was linearized with NgoMI (New England Biolabs), and the pUC18 plasmid (2.7 kb) with XmaI (New England Biolabs). These enzymes yield compatible cohesive ends, but after ligation the new site can not be cut with either of them. The pBS.CMVLux fragment was dephosphorylated by calf intestinal alkaline phosphatase (CIP, New England Biolabs). Then it was either rhodamine labeled using RCl and TRITC to be used for microscopic studies, or was used unlabeled for expression studies. The pUC18 fragment was either conjugated to CPI-NLS or to CPI-DNLS at 0.8:1 peptide to DNA weight ratio, or was used unmodified. The two fragments were ligated with the FastLink ligation kit (Epicentre, Madison, Wis.) at 4.5-fold molar excess of the pUC18 fragment. The T4 DNA ligase enzyme provided in the kit was diluted 40-fold in NEBuffer 4 (New England Biolabs) and was added to the ligation at 1 µl/1 µg DNA. 10 Unit/1 tig DNA XmaI enzyme was also added. The reaction was incubated in a PTC-200 Peltier Thermal Cycler (MJ Research) for four cycles of 30 min at 25° C. and 30 min at 37° C. Both enzymes were replenished after the second cycle. The reaction ended with incubation at 25° C. for 30 min. This cycling between ligation and digestion helped to consume about 95% of the linear expression vector. Half of the ligation mixtures did not receive the enzymes and were saved as unligated controls. The efficiency of the ligation was assessed by agarose gel electrophoresis using HindIII digested λ DNA (Life Technologies) and Hi-Lo DNA Markers (Minnesota Molecular) as molecular size standards.

Expression Studies—The TNT Coupled Reticulocyte Lysate System (Promega Corp.) was used for in vitro luciferase expression from the T7 promoter that is within pBS.CMV-Lux. The manufacturer's protocol was modified so that only one quarter of the recommended reaction volume was used and only 14 fmole template was added. After 2 hrs of incubation at 30° C., 1 µl of each reaction was assayed for luciferase activity as described (de Wet, J. R., Wood, K. V., DeLuca, M., Helinski, D. R. and Subramani, S. 1987. Firefly luciferase gene: structure and expression in mammalian cells. *Mol. Cell. Biol.* 7:725–737.). For in vivo expression studies, luciferase activity was measured 15 or 40 hours after cells were transfected with 2 µg total DNA/well (containing approximately 100 fmole expression vector) using Lipofectin (Life Technologies) or LT-1 (PanVera, Madison, Wis.). DNA samples were also microinjected into the cytoplasm of HeLa cells as previously described (Dowty, M. E., Williams, P., Zhang, G. and Wolff, J. A. 1995. Plasmid DNA entry into post-mitotic nuclei of primary rat myotubes. *Proc. Natl. Acad. Sci. USA* 92:4572–4576.). Luciferase activity was assayed 4 hrs after 200 cells were microinjected with samples containing 100 fmole/µl expression vector. For all the luciferase expression studies, total luciferase levels were calculated by multiplying the relative light units (RLU) in the analyzed samples by their respective dilution factors without accounting for quenching.

Figure 6A:
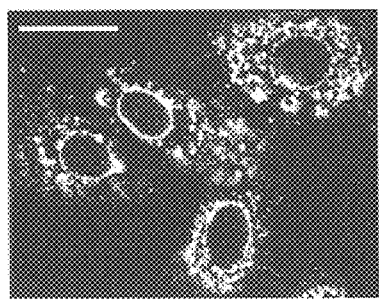
FIGS. 6A–6I illustrate expression from linear ligated DNA.

Results:

The covalent attachment of hundreds of peptides to pDNA completely abolished transcription of the marker gene. This effect was expected based on the nature of the cross-linking and based on previous works done with CC-1065 (Sun, D. and Hurley, L. H. 1992. Effect of the (+)-CC-1065-(N3-adenine)DNA adduct on in vitro DNA synthesis mediated by Escherichia coli DNA polymerase. Biochem. 31:2822–2829.). To avoid this adverse effect, a NLS conjugated linear pUC18 DNA fragment was ligated to an unmodified linear pBS.CMVLux DNA fragment (which contains both the CMV and T7 promoter 5' to the firefly luciferase gene). Gel electrophoresis of the ligation products confirmed that the majority (estimated 95%) of the expression vector became ligated to the pUC18 fragment (FIG. 6A, lanes 2, 4 and 6). [A. Electrophoresis of ligated samples on a 0.5% agarose gel. Each lane contains 130 ng NgoMI cut linear, CIP treated pBS.CMVLux DNA (1): self ligated; (2): ligated to unmodified, linear pUC18; (3): as lane 2, unligated control; (4): ligated to NLS-conjugated pUC18; (5): as lane 4, unligated control; (6): ligated to DNLS-conjugated pUC18; (7): as lane 6, unligated control. Lane 8 shows Hi-Lo DNA Markers and lane 9 has HindIII digested λ phage DNA. The arrow points at the linear pBS.CMVLux (6.1 kb). The filled arrowhead designates the unmodified linear pUC18 (2.7 kb). The open arrowhead indicates the peptide conjugated pUC18 (migrating as a>5 kb fragment).] In the self-ligation control (FIG. 6A, lane 1) and in the unligated control mixtures (FIG. 6A, lanes 3, 5 and 7) the amount and the gel-mobility of the pBS.CMVLux expression fragment did not change during incubation.

Figure 5A:
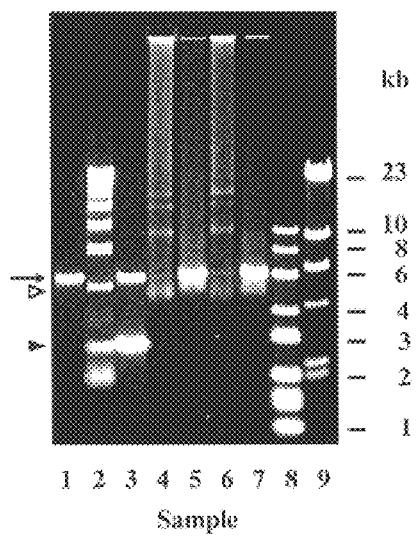
FIGS. 5A–5B illustrate nuclear transport of linear ligated DNA.
Figure 5B:
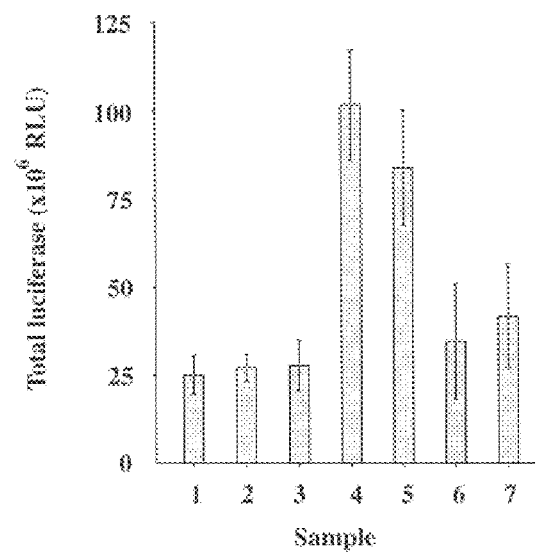

In order to confirm that the ligated product is also imported into the nucleus the pBS.CMVLux fragment was rhodamine labeled prior to ligation. Import assays in digitonin permeabilized cells showed some rare nuclear spots even with the unligated control, but the number of these spots and their intensity was significantly increased when the fragments were covalently coupled (FIG. 5). [Confocal images of central optical sections of digitonin permeabilized HeLa cells incubated for 1 hr at 37° C. in the presence of RRL with a mixture of 6.1 kb linear Rh-DNA and 2.7 kb linear NLS-conjugated DNA fragment either unligated (A) or ligated (B). Scale bars: 20 µm.] This suggests that the NLS-peptides on the pUC18 DNA fragment provided sufficient signal to support the nuclear uptake of the whole molecule.

The level of in vitro T7 promoter-driven luciferase expression from self ligated linear pBS.CMVLux DNA (sample 1 from FIG. 6) was compared to expression from the same pBS.CMVLux fragment that was ligated to unmodified (sample 2), NLS-peptide conjugated (sample 4), or DNLS-peptide conjugated (sample 6) linear pUC18 DNA. In vitro transcription and translation assays yielded 3 to $7 \times 10^7$ RLU in all samples. The presence of the positively charged peptides 1–2 kb away from the expression cassette did not inhibit the T7 RNA polymerase.

Figure 6B:
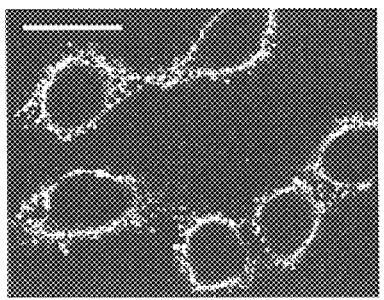
Figure 6C:
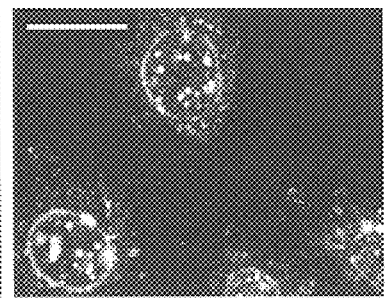
Figure 6D:
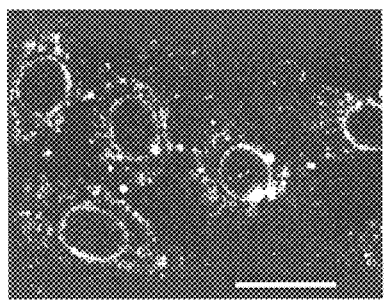
Figure 6E:
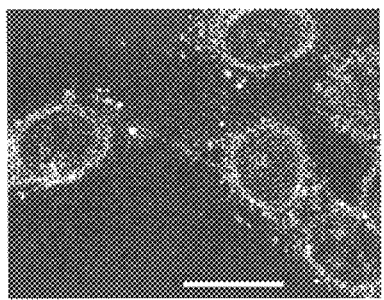
Figure 6F:
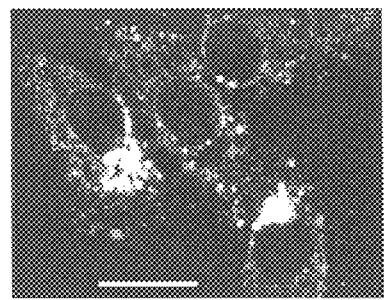
Figure 6G:
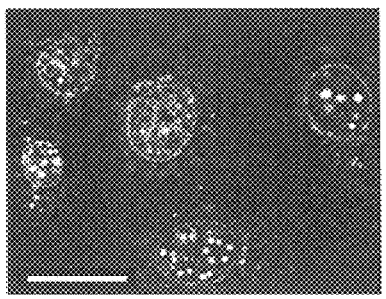
Figure 6H:
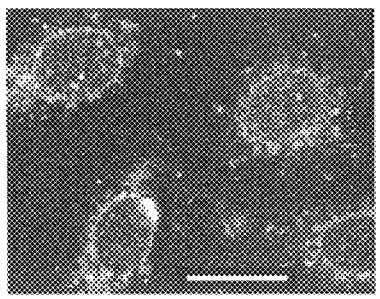
Figure 6I:
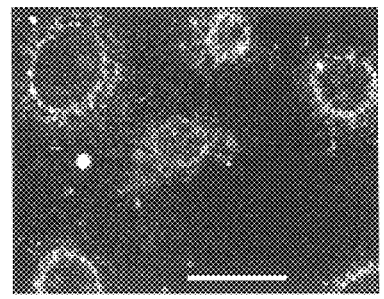

The in vivo luciferase expression of pBS.CMVLux DNA ligated to peptide conjugated pUC18 was assessed after transfection or microinjection experiments into NIH 3T3 and HeLa cells in culture. The same linear pBS.CMVLux samples (self-ligated or pUC18-ligated, and unligated controls) were used as for the in vitro transcription studies above. After transfecting HeLa cells with equal molar amounts of the different DNA samples using cationic liposome formulations the cell lysates were assayed for luciferase activity (FIG. 6B). [B. DNA samples (1–7 from panel A) containing equimolar amounts of the expression vector were transfected into HeLa cells using LT-1 liposomes. Complexes were formed in triplicate for each sample. 15 hrs later the luciferase activity was assayed. The mean and standard deviation of the total relative light units are presented. Similar results were obtained after three other transfections with LT-1 and also with Lipofectin.] The presence of the wild type NLS peptide (FIG. 6B, sample 4) caused a slight but insignificant increase in expression above the no-ligase control (FIG. 6B, sample 5). The 2 to 3 fold greater expression of the unligated or ligated, wild type NLS samples (FIG. 6B, samples 4 and 5) above the controls (FIG. 6B, samples 1–3) may rather be due to an effect of the cationic NLS peptide on the transfection process prior to nuclear transport. Therefore microinjection was also used to deliver ligated DNA samples directly into the cytoplasm of HeLa cells. Microinjection of the pBS.CMVLux ligated to NLS or DNLS peptide-conjugated pUC18 fragment resulted in 5 to 20 fold lower luciferase levels than the self-ligated control ($4 \times 10^3$ and $1 \times 10^3$ RLU for samples 4 and 6 compared to $2 \times 10^4$ RLU for sample 1 from FIG. 6). These in results show that chemically modified DNA can be expressed in mammalian cells.

Conclusions:

This demonstrates that the covalent modification of DNA with a signal peptide alters its cellular transport behavior and interaction with other cellular factors and that the DNA can still be expressed.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A method for enhancing gene delivery to a cell for expression, comprising:
   a) preparing a nucleic acid molecule comprising a gene, the gene having a beginning nucleotide and an ending nucleotide;
   b) covalently attaching a cellular transport enhancing signal to the nucleic acid molecule, for directing the nucleic acid molecule to a target location, wherein said covalently attaching does not include biotinylated DNA, and wherein the signal: 1) is not directly attached to a nucleotide between the beginning and ending nucleotides of the gene; and 2) does not prevent gene expression; and,
   c) delivering the nucleic acid molecule to a cell wherein the gene is expressed.

2. The method of claim 1 wherein the cellular transport enhancing signal is selected from the group consisting of a nuclear localizing signal, a ligand that binds a cellular receptor, and a releasing signal.

3. The method of claim 1 wherein the step of covalently attaching comprises modifying the nucleic acid molecule using an alkylating molecule.

4. The method of claim 3 wherein the alkylating molecule is selected from the group consisting of a mustard and a molecule having a ring containing 3 carbon atoms.

5. The method of claim 4 wherein the mustard is selected from the group consisting of a nitrogen mustard and a sulfur mustard.

6. The method of claim 4 wherein the molecule having a ring containing 3 carbon atoms is selected from the group consisting of aziridines, oxiranes, cyclopropanes, activated cyclopropanes, and episulfides.

7. The method of claim 6 wherein the nitrogen mustard consists of an R-chloride derivative.

8. The method of claim 4 wherein the molecule having a ring containing 3 carbon atoms consists of a CPI moiety.

9. The method of claim 1 wherein the gene consists of double-stranded DNA.

10. A covalently modified nucleic acid that is delivered to a cell for expression of a gene, comprising:
    a) a nucleic acid molecule comprising the gene, the gene having a beginning nucleotide and an ending nucleotide; and,
    b) a cellular transport enhancing signal covalently attached to the nucleic acid molecule, for directing the nucleic acid molecule to a target location, and for enhancing gene transport and cellular expression, wherein said covalently attaching does not include biotinylated DNA, and wherein the signal: 1) is not directly attached to a nucleotide between the beginning and ending nucleotides of the gene; and 2) does not prevent gene expression.

11. The nucleic acid of claim 10 wherein the cellular transport enhancing signal is selected from the group consisting of a nuclear localizing signal, a ligand that binds a cellular receptor, and a releasing signal.

12. The nucleic acid of claim 10 wherein the cellular transport enhancing signal is covalently attached to the nucleic acid molecule by an alkylating molecule.

13. The nucleic acid of claim 12 wherein the alkylating molecule is selected from the group consisting of a mustard and a molecule having a ring containing 3 carbon atoms.

14. The nucleic acid of claim 13 wherein the mustard is selected from the group consisting of a nitrogen mustard and a sulfur mustard.

15. The nucleic acid of claim 13 wherein the molecule having a ring containing 3 carbon atoms is selected from the group consisting of aziridines, oxiranes, cyclopropranes, activated cyclopropranes, and episulfides.

16. The nucleic acid of claim 14 wherein the nitrogen mustard consists of an R-chloride derivative.

17. The nucleic acid of claim 13 wherein the molecule having a ring containing 3 carbon atoms consists of a CPI moiety.

18. The nucleic acid of claim 10 wherein the gene consists of double-stranded DNA.

\* \* \* \* \*

SEQUENCE LISTING

```
<160> NUMBER OF SEQ ID NOS: 11

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence:CONTAINS
      SEQUENCES FROM THE  SV40 GENOME

<400> SEQUENCE: 1

Cys Lys Lys Lys Ser Ser Ser Asp Asp Glu Ala Thr Ala Asp Ser Gln
  1               5                  10                  15

His Ser Thr Pro Pro Lys Lys Lys Arg Lys Val Glu Asp Pro Lys Asp
             20                  25                  30

Phe Pro Ser Glu Leu Leu Ser
         35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence:CONTAINS
      SEQUENCES FROM THE SV40 GENOME

<400> SEQUENCE: 2

Cys Lys Lys Lys Trp Asp Asp Glu Ala Thr Ala Asp Ser Gln His Ser
  1               5                  10                  15

Thr Pro Pro Lys Lys Lys Arg Lys Val Glu Asp Pro Lys Asp Phe Pro
             20                  25                  30

Ser Glu Leu Leu Ser
         35

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence:CONTAINS
      SEQUENCES FROM THE  HUMAN HETEROGENEOUS NUCLEAR
      RIBONUCLEOPROTEIN

<400> SEQUENCE: 3
```

Cys Tyr Asn Asp Phe Gly Asn Tyr Asn Asn Gln Ser Ser Asn Phe Gly
 1               5                  10                  15

Pro Met Lys Gln Gly Asn Phe Gly Gly Arg Ser Ser Gly Pro Tyr
            20                  25                  30

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:CONTAINS
      SEQUENCES FROM THE HUMAN ADENOVIRUS TYPE 2 E1A
      PROTEIN

<400> SEQUENCE: 4

Cys Lys Arg Gly Pro Lys Arg Pro Arg Pro
 1               5                  10

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence:CONTAINS
      SEQUENCES FROM THE XENOPUS LEAVIS NUCLEOPLASMIN
      PROTEIN

<400> SEQUENCE: 5

Cys Lys Lys Ala Val Lys Arg Pro Ala Ala Thr Lys Lys Ala Gly Gln
 1               5                  10                  15

Ala Lys Lys Lys Lys Leu
            20

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:CONTAINS
      SEQUENCES FROM THE HUMAN C-MYC ONCOGENE

<400> SEQUENCE: 6

Cys Lys Lys Lys Gly Pro Ala Ala Lys Arg Val Lys Leu Asp
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: CONTAINS
      SEQUENCES FROM THE SV40 GENOME

<400> SEQUENCE: 7

Cys Gly Tyr Lys Lys Arg Lys Val Gly Gly
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:SV40 large T
      antigen NLS

<400> SEQUENCE: 8

-continued

```
Cys Gly Tyr Gly Pro Lys Lys Lys Arg Lys Val Gly Gly
 1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:SV40 NLS
      (mNLS)

<400> SEQUENCE: 9

Cys Gly Tyr Gly Pro Lys Asp Lys Arg Lys Val Gly Gly
 1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:SV40 NLS
      (rNLS)

<400> SEQUENCE: 10

Cys Gly Lys Gly Lys Pro Arg Lys Val Lys Tyr Gly Trp
 1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:OLIGO-LYSINE

<400> SEQUENCE: 11

Cys Lys Lys Trp Lys Lys Lys Gly
 1               5
```